(12) United States Patent
Haupts

(10) Patent No.: US 9,579,285 B2
(45) Date of Patent: Feb. 28, 2017

(54) PREPARATION OF A POWDERY PHARMACEUTICAL COMPOSITION BY MEANS OF AN EXTRUDER

(75) Inventor: Marcel Haupts, Stolberg (DE)

(73) Assignee: GRUENENTHAL GMBH, Aachen (DE)

( * ) Notice: Subject to any disclaimer, the term of this patent is extended or adjusted under 35 U.S.C. 154(b) by 132 days.

(21) Appl. No.: 13/018,629

(22) Filed: Feb. 1, 2011

(65) Prior Publication Data

US 2011/0187017 A1    Aug. 4, 2011

Related U.S. Application Data

(60) Provisional application No. 61/300,857, filed on Feb. 3, 2010.

(30) Foreign Application Priority Data

Feb. 3, 2010    (EP) ..................................... 10001095

(51) Int. Cl.
    *A61K 9/14*    (2006.01)

(52) U.S. Cl.
    CPC .................................. *A61K 9/146* (2013.01)

(58) Field of Classification Search
    CPC .................................................... A61K 9/146
    USPC ....................................................... 264/140
    See application file for complete search history.

(56) References Cited

U.S. PATENT DOCUMENTS

| | | |
|---|---|---|
| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,207,893 A | 6/1980 | Michaels |
| 4,343,789 A | 8/1982 | Kawata et al. |
| 4,353,887 A | 10/1982 | Hess |
| 4,404,183 A | 9/1983 | Kawata et al. |
| 4,427,681 A | 1/1984 | Munshi et al. |

(Continued)

FOREIGN PATENT DOCUMENTS

| | | |
|---|---|---|
| CA | 2414349 A1 | 1/2002 |
| CA | 2503155 A1 | 5/2004 |

(Continued)

OTHER PUBLICATIONS

European Search Report, Application No./Patent No. 12003743.7-1219, Sep. 24, 2012.

(Continued)

*Primary Examiner* — Larry Thrower
(74) *Attorney, Agent, or Firm* — Norris McLaughlin & Marcus, P.A.

(57) ABSTRACT

The invention relates to a method for the preparation of a powdery pharmaceutical composition comprising a pharmaceutical excipient and a pharmaceutical component, the method comprising the step of extruding a mixture of the pharmaceutical excipient and the pharmaceutical component in an extruder at a temperature profile allowing a liquid melt of the mixture to congeal in the extruder and to exit the extruder in form of a powder.

11 Claims, 5 Drawing Sheets

(56) References Cited

U.S. PATENT DOCUMENTS

Figure 1:
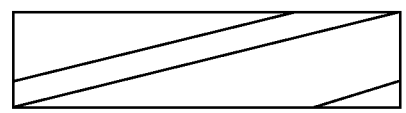
Figure 1:
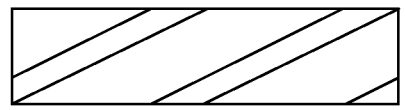
Figure 1:
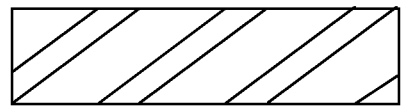

| | | |
|---|---|---|
| 4,457,933 A | 7/1984 | Gordon et al. |
| 4,462,941 A | 7/1984 | Lee et al. |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,713,243 A | 12/1987 | Schiraldi et al. |
| 4,744,976 A | 5/1988 | Snipes et al. |
| 4,764,378 A | 8/1988 | Keith et al. |
| 4,765,989 A | 8/1988 | Wong et al. |
| 4,774,074 A | 9/1988 | Snipes |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk et al. |
| 4,940,556 A | 7/1990 | MacFarlane et al. |
| 4,957,668 A | 9/1990 | Placard |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,073,379 A | 12/1991 | Klimesch et al. |
| 5,082,668 A | 1/1992 | Wong et al. |
| 5,169,645 A | 12/1992 | Shukla et al. |
| 5,198,226 A | 3/1993 | MacFarlane et al. |
| 5,200,197 A | 4/1993 | Wright et al. |
| 5,211,892 A | 5/1993 | Gueret |
| 5,273,758 A | 12/1993 | Royce |
| 5,350,741 A | 9/1994 | Takada |
| 5,378,462 A | 1/1995 | Boedecker et al. |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,556,640 A | 9/1996 | Ito et al. |
| 5,601,842 A | 2/1997 | Bartholomaeus |
| 5,681,517 A | 10/1997 | Metzger |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,916,584 A | 6/1999 | O'Donoghue et al. |
| 5,928,739 A | 7/1999 | Pophusen et al. |
| 5,945,125 A | 8/1999 | Kim |
| 5,948,787 A | 9/1999 | Merrill et al. |
| 5,968,925 A | 10/1999 | Knidlberger |
| 6,009,390 A | 12/1999 | Gupta et al. |
| 6,009,690 A | 1/2000 | Rosenberg et al. |
| 6,077,538 A | 6/2000 | Merrill et al. |
| 6,096,339 A | 8/2000 | Ayer et al. |
| 6,117,453 A | 9/2000 | Seth et al. |
| 6,133,241 A | 10/2000 | Bok et al. |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,261,599 B1 * | 7/2001 | Oshlack et al. ............ 424/457 |
| 6,306,438 B1 | 10/2001 | Oshlack et al. |
| 6,309,668 B1 | 10/2001 | Bastin et al. |
| 6,337,319 B1 | 1/2002 | Wang |
| 6,340,475 B2 | 1/2002 | Shell et al. |
| 6,344,535 B1 | 2/2002 | Timmermann et al. |
| 6,387,995 B1 | 5/2002 | Sojka |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,997 B1 | 4/2003 | Breitenbach et al. |
| 6,592,901 B2 | 7/2003 | Durig et al. |
| 6,635,280 B2 | 10/2003 | Shell et al. |
| 6,699,503 B1 | 3/2004 | Sako et al. |
| 6,723,340 B2 | 4/2004 | Gusler et al. |
| 6,733,783 B2 | 5/2004 | Oshlack et al. |
| 7,141,250 B2 | 11/2006 | Oshlack et al. |
| 7,176,251 B1 | 2/2007 | Bastioli et al. |
| 7,300,668 B2 | 11/2007 | Pryce et al. |
| 7,776,314 B2 | 8/2010 | Bartholomaus et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0187192 A1 | 12/2002 | Joshi et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0031546 A1 | 2/2003 | Araki et al. |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068392 A1 | 4/2003 | Sackler |
| 2003/0091630 A1 | 5/2003 | Louie-Helm et al. |
| 2003/0104052 A1 | 6/2003 | Berner et al. |
| 2003/0118641 A1 | 6/2003 | Maloney et al. |
| 2003/0124185 A1 | 7/2003 | Oshlack et al. |
| 2003/0129230 A1 | 7/2003 | Baichwal et al. |
| 2003/0133985 A1 | 7/2003 | Louie-Helm et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0081694 A1 | 4/2004 | Oshlack et al. |
| 2004/0091528 A1 | 5/2004 | Rogers et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0214223 A1 | 9/2005 | Bartholomaeus et al. |
| 2005/0236741 A1 | 10/2005 | Arkenau et al. |
| 2005/0266084 A1 | 12/2005 | Li et al. |
| 2006/0002859 A1 | 1/2006 | Arkenau-Maric et al. |
| 2006/0002860 A1 | 1/2006 | Bartholomaus et al. |
| 2006/0039864 A1 | 2/2006 | Bartholomaeus et al. |
| 2006/0073102 A1 | 4/2006 | Huaihung et al. |
| 2006/0099250 A1 | 5/2006 | Tian et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Arkenau-Maric et al. |
| 2006/0194826 A1 | 8/2006 | Oshlack et al. |
| 2006/0240110 A1 | 10/2006 | Kiick et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 * | 8/2007 | Gregory et al. ............ 424/489 |

(56) References Cited

U.S. PATENT DOCUMENTS

| | | |
|---|---|---|
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0259045 A1 | 11/2007 | Mannion et al. |
| 2007/0264327 A1 | 11/2007 | Kumar et al. |
| 2008/0063725 A1 | 3/2008 | Guimberteau et al. |
| 2008/0081290 A1 | 4/2008 | Wada et al. |
| 2008/0145429 A1 | 6/2008 | Leyendecker et al. |
| 2008/0220079 A1 | 9/2008 | Chen |
| 2008/0247959 A1 | 10/2008 | Bartholomaus et al. |
| 2008/0248113 A1 | 10/2008 | Bartholomaus et al. |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0312264 A1 | 12/2008 | Arkenau-Maric et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0081290 A1 | 3/2009 | McKenna et al. |
| 2009/0202634 A1 | 8/2009 | Jans et al. |
| 2009/0232887 A1 | 9/2009 | Odidi et al. |
| 2010/0015223 A1 | 1/2010 | Cailly-Dufestel et al. |
| 2010/0098758 A1 | 4/2010 | Bartholomus et al. |
| 2010/0151028 A1 | 6/2010 | Ashworth et al. |
| 2010/0221322 A1 | 9/2010 | Bartholomus et al. |
| 2010/0249045 A1 | 9/2010 | Babul |
| 2010/0260833 A1 | 10/2010 | Bartholomus et al. |
| 2010/0280047 A1 | 11/2010 | Kolter et al. |
| 2011/0020451 A1 | 1/2011 | Bartholomaus et al. |
| 2011/0038930 A1 | 2/2011 | Barnscheid et al. |
| 2011/0082214 A1 | 4/2011 | Faure et al. |
| 2011/0092515 A1* | 4/2011 | Qiu et al. ............... 514/253.06 |
| 2012/0141583 A1 | 6/2012 | Mannion et al. |
| 2012/0225901 A1 | 9/2012 | Leyendecker et al. |
| 2014/0094481 A1 | 4/2014 | Fleischer et al. |

FOREIGN PATENT DOCUMENTS

| | | |
|---|---|---|
| CA | 2489855 A1 | 4/2005 |
| DE | 195 22 899 C1 | 12/1996 |
| EP | 0 043 254 1 A | 1/1982 |
| EP | 0 229 652 A2 | 7/1987 |
| EP | 0 641 195 A | 3/1995 |
| EP | 2402004 A2 | 1/2012 |
| GB | 1 147 210 A | 4/1969 |
| KR | 20090085312 A | 8/2009 |
| RU | 2198197 C2 | 2/2003 |
| RU | 2326654 C2 | 9/2005 |
| WO | 95/17174 A1 | 6/1995 |
| WO | 96/03979 A1 | 2/1996 |
| WO | 98/35655 A2 | 8/1998 |
| WO | WO 98/51758 A1 | 11/1998 |
| WO | WO 2004/026280 A2 | 4/2004 |
| WO | WO 2004/078212 A1 | 9/2004 |
| WO | 2004 098567 A2 | 11/2004 |
| WO | 2005/016313 A1 | 2/2005 |
| WO | 2005016314 A1 | 2/2005 |
| WO | 2005/063214 A1 | 7/2005 |
| WO | 2005 079760 A1 | 9/2005 |
| WO | 2005/102286 A1 | 11/2005 |
| WO | 2005105036 A1 | 11/2005 |
| WO | 2006/002883 A1 | 1/2006 |
| WO | 2006/002884 A1 | 1/2006 |
| WO | 2006/002886 A1 | 1/2006 |
| WO | 2006/082097 A1 | 8/2006 |
| WO | 2006/082099 A1 | 8/2006 |
| WO | WO 2007/112286 A2 | 10/2007 |
| WO | 2008 023261 A1 | 2/2008 |
| WO | 2008/107149 A2 | 9/2008 |
| WO | 2009/092601 A1 | 7/2009 |
| WO | 2009/135680 A1 | 11/2009 |
| WO | 2010057036 A2 | 5/2010 |

OTHER PUBLICATIONS

Henrist et al. In vitro and in vivo evaluation of starch-based hot stage extruded double matrix systems. Journal of Controlled Release. 2001, vol. 75, pp. 391-400.

McNeill et al. Properties controlling the diffusion and release of water-soluble solutes from poly(ethylene oxide) hydrogels. 4. Extended constant rate release from partly-coated spheres. Journal Biomat. Sci. Polym. Ed. 1996, vol. 7, pp. 953-963.

Pillay et al. A novel approach for constant rate delivery of highly soluble bioactives from a simple monolithic system. Journal of Controlled Release. 2000, vol. 67, pp. 67-78.

João F. Pinto et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).

European Search Report of related EP Application No. 12 00 2708 dated Sep. 24, 2012.

Tranquilan-Aranilla et al., "Kappa-carrageenan-polyethylene oxide hydrogel blends prepared by gamma irradiation," Radiation Physics and Chemistry vol. 55, pp. 127-131, 1999.

PCT International Search Report and Written Opinion for PCT Application No. PCT/EP2013/057851 dated Jun. 12, 2013.

Lenindzer, A., "The molecular basis of the structure and functions of cells" Moscow 1974, p. 68.

Kondrat, T., "Technology dosage forms" Moscow 1991, p. 96.

Moorman-Li, R. et al, "A Review of Abuse-Deterrent Opioids for Chronic Nonmalignant Pain." Pharmacy and Therapeutics, vol. 37 No. 7, Jul. 2012, pp. 412-421.

Eudragit NE40D web page from Evonik website; downloaded Feb. 24, 2015.

Eudragit RS PO web page from Evonik website; downloaded Feb. 24, 2015.

Glyceryl behenate monograph; European Pharmacopeia 5.0; dated Jan. 2005;.downloaded Feb. 24, 2015.

PCT International Search Report and Written Opinion for PCT Application No. PCT/EP2014/0777748 dated Feb. 12, 2015.

* cited by examiner

A

B

C

A)

B)

C)

PREPARATION OF A POWDERY PHARMACEUTICAL COMPOSITION BY MEANS OF AN EXTRUDER

The invention relates to a method for the preparation of a powdery pharmaceutical composition comprising a pharmaceutical excipient, preferably a first pharmaceutical excipient, and a pharmaceutical component, preferably a second pharmaceutical excipient or a pharmacologically active substance, optionally together with a third constituent, preferably another pharmaceutical excipient, the method comprising the step of extruding a mixture of the pharmaceutical excipient and the pharmaceutical component in an extruder at a temperature profile allowing a liquid melt of the mixture to congeal in the extruder and to exit the extruder in form of a powder. The powder is particularly useful in the manufacture of pharmaceutical dosage forms comprising at least one pharmacologically active substance. The invention further relates to a method for the manufacture of pharmaceutical dosage forms, such as tablets.

Many pharmaceutical dosage forms require homogeneous distribution of all excipients. Homogeneous distribution of excipients is required in order to maintain product quality, not only with respect to changeless drug content, but also with respect to changeless properties which are based on the presence of specific amounts of excipients such as storage stability, processability, disintegration, release profile, and the like.

Homogeneous distribution of excipients is usually achieved by vigorously mixing the excipients prior to forming the dosage form e.g. by subsequent granulation or direct compression. Blending excipients in a mixer is the method of choice for solid excipients. If one or more excipients are liquid or pasty, however, blending is more difficult to achieve, especially if the compatibility of excipients is limited, e.g. because one excipient is hydrophilic and the other excipient is hydrophobic.

Particular problems arise when the individual amounts of excipients to be mixed with one another substantially differ from one another. For example, it is rather difficult to homogenously distribute small amounts of hydrophobic liquids, e.g. 0.5 wt.-% in a solid mixture of hydrophilic excipients.

For example, α-tocopherol, which is a hydrophobic oily liquid at ambient temperature, is extensively used as antioxidant in pharmaceutical dosage forms. It is known to use α-tocopherol as a pre-blend with other pharmaceutical excipients in order to better distribute the comparatively small amount (e.g. 0.1 to 0.2 wt.-%) of α-tocopherol in the overall dosage form. Pre-blends of hydrophobic α-tocopherol with hydrophilic polyethylene glycol are commercially available. Such products are typically manufactured by spray-congealing. A melt of polyethylene glycol is homogenized with α-tocopherol and is sprayed into a drying-tower that is cooled by nitrogen gas and the congealed particles are collected. Spray congealing technology is very laborious and costly.

GB-A 1,147,210 relates to a process for making a dry, free flowing, finely divided, fat-soluble vitamin-active product, comprising (1) preparing a colloidal solution of cold water dispersible, non-gelling colloid material and water; (2) dispersing in said colloidal solution a water insoluble, fat soluble vitamin active composition to form a first dispersion; (3) dispersing the latter in a water immiscible liquid dispersing medium to form a second dispersion; (4) extracting water at −10 to 0° C. from the latter with a water extraction agent until droplets of the first dispersion solidify to form particles; (5) separating the latter from the dispersing medium and water extraction agent at −10 to 0° C.; and (6) removing residual moisture from the solid particles.

U.S. Pat. No. 4,603,143 discloses the preparation of free-flowing and stable vitamin-active powders utilizing special silicon-containing materials which are predominately in the form of substantially discrete agglomerates.

U.S. Pat. No. 4,892,889 relates to a process for making a directly-compressible vitamin powder utilizing a conventional spray-dryer. The resulting powder is comprised of a fat-soluble vitamin, a water-soluble carbohydrate, and a gelatin having a bloom number between 30 and 300.

U.S. Pat. No. 6,261,599 and US 2004/0081694 disclose sustained release oral opioid analgesic dosage forms comprising a plurality of multiparticulates produced via melt extrusion techniques. The extruded material exits the extruder in form of an extruded strand.

DE 195 22 899 discloses a method for continuously sintering a granulate for the manufacture of compressed articles, particularly for tableted drug formulations. None of the components is melted in the extruder and no strand is extruded.

EP-A 0 043 254 discloses a pharmaceutical composition with a retarded liberation of an active material and a process for producing the same. An active material in finely divided form is mixed with both a finely divided high melting lipid or lipoid component and a finely divided low melting lipid or lipoid component, the resulting mixture is brought to a temperature which is above the melting point of the low melting component but below the melting point of the high melting component and the mixture, after melting of the low melting component, is allowed to cool to below the melting point thereof and subsequently worked up to give a finished pharmaceutical composition which has a controlled retarded liberation and which is safe, easy and not expensive to produce.

EP-A 229 652 discloses that certain acid compounds stabilize the potency of vitamin E compounds when processed into a dry particulate free-flowing form. A potency stabilized composition in a dry, particulate, free-flowing form is comprised of Vitamin E incorporated in a carrier whose potency has been stabilized with an effective amount of a certain acid compound. Such potency stabilizing acid compounds are hydroxy acids or amino acids, such as citric acid, ascorbic acid, methionine and cysteine.

EP-A 641 195 relates to a continuous method for the production of retarded pharmaceutical compositions by an extrusion process. A mixture of an active material, a low and high melting lipid or lipoid components is introduced by means of an extruder screw conveyor into a preheated extruder and brought to a temperature which is at most about 4° C. above the melting temperature of the low melting component at a pressure of about 200 to about 600 kPa (N/m$^2$). The mass is extruded through a nozzle plate with a nozzle diameter of about 1.2 to about 4 mm and subsequently cooled, and if desired, granulated.

WO 95/17174 discloses a process for making an ingestible, neutral tasting laxative composition by coating dioctyl sulfosuccinate with a material selected from the group consisting of $C_{14-18}$ fats, $C_{16-20}$ fatty acids, sucrose polyesters, $C_{14-18}$ fats and waxes, pH sensitive polymers, food gums, and combinations thereof. Preferably, two successive, different coatings are applied to the dioctyl sulfosuccinate by steps including either fluid bed coating, spray congealing, spray quenching, or spray drying.

WO 96/03979 relates to an apparatus and method for preparing solid forms with controlled release of the active ingredient according to the spray drying and spray congealing techniques by means of an atomizer utilizing the mechanical vibrations of resonant metal elements or nozzles so as to obtain very small droplets with very short spray length.

WO 98/35655 discloses a method of physically separating at least two active substances A and B in solid medicament forms, wherein a melting process is applied and active substance A is homogeneously intermingled with the higher-melting lipids or lipoid constituent and the mixture thus obtained is granulated or finely divided in another manner.

WO 2009/135680 relates to a process for preparing a powder comprising the steps of providing at least one first component being in liquid form or having a waxy consistency at ambient temperature, providing at least one second component having a melting point or melting point/range in the range from above ambient temperature to below the degradation temperature of said first component, forming a homogenous liquid mixture comprising said at least one first component and said at least one second component by stirring and heating the mixture to or keeping the mixture at a temperature in the range from above the melting point or melting point/range of said second component and below the degradation temperature of said first component, transferring the liquid mixture to at least one spray congealing unit by at least one transfer unit, which is adapted to keep the mixture in its liquid form during its transfer, spray congealing said mixture, and isolating the powder obtained upon spray congealing.

The aforementioned established procedures, however, are not satisfactory in every respect. With some procedures, generally only large amounts of excipients can be employed, other procedures are quite laborious and require sophisticated equipment. There is a demand for simple and effective methods to continuously and homogenously incorporate incompatible pharmaceutical excipients in substantially differing amounts into pharmaceutical compositions.

It is an object of the invention to provide methods for the preparation of powdery pharmaceutical compositions comprising a homogeneous mixture of at least two pharmaceutical excipients and having advantages over the methods of the prior art. The manufacture of the powdery pharmaceutical compositions should proceed easily by means of standard equipment, should be possible in a continuous fashion and should encompass a limited number of method steps only.

This object has been achieved by the subject-matter of the patent claims.

The invention relates to a method for the preparation of a powdery pharmaceutical composition comprising a pharmaceutical excipient, preferably first pharmaceutical excipient, more preferably polyalkylene glycol, and a pharmaceutical component, preferably a second pharmaceutical excipient or a pharmacologically active substance (drug), more preferably α-tocopherol; optionally together with a third constituent, preferably another pharmaceutical excipient; the method comprising the step of extruding a mixture of the pharmaceutical excipient, preferably first pharmaceutical excipient, more preferably polyalkylene glycol, and the pharmaceutical component, preferably second pharmaceutical excipient or pharmacologically active substance (drug), more preferably α-tocopherol, in an extruder at a temperature profile allowing a liquid melt of the mixture to congeal in the extruder and to exit the extruder in form of a powder.

It has been surprisingly found that incompatible pharmaceutical excipients and components, respectively, e.g. a hydrophilic pharmaceutical excipient, preferably first pharmaceutical excipient, more preferably polyalkylene glycol, and a hydrophobic pharmaceutical component, preferably second pharmaceutical excipient, more preferably α-tocopherol, can be homogeneously mixed with one another and converted into a powdery pharmaceutical composition in a simple extrusion process, typically without the requirement of subsequently grinding the material that exits the extruder.

By the method according to the invention homogeneously mixed powdery pharmaceutical compositions can even be obtained when the amount of the excipient and the component substantially differs from one another, e.g. when the pharmaceutical excipient is present in an amount of 99 wt.-% or more and the pharmaceutical component is present in an amount of 1 wt.-% or less, both percentages being related to the total weight of the powdery pharmaceutical composition. The present invention provides a simple process that can be reduced to practice by means of conventional tabletting equipment.

A first aspect of the invention relates to a method for the preparation of a powdery pharmaceutical composition comprising a pharmaceutical excipient, preferably first pharmaceutical excipient, more preferably polyalkylene glycol, and a pharmaceutical component, preferably second pharmaceutical excipient, more preferably α-tocopherol; the method comprising the step of (b) extruding a mixture of the pharmaceutical excipient, preferably first pharmaceutical excipient, more preferably polyalkylene glycol, and the pharmaceutical component, preferably second pharmaceutical excipient, more preferably α-tocopherol, in an extruder at a temperature profile allowing a liquid melt of the mixture to congeal in the extruder and to exit the extruder in form of a powder.

In a preferred embodiment, the mixture comprises a third constituent, preferably an another, i.e. additional pharmaceutical excipient.

For the purpose of the specification, a "pharmaceutical composition" is any composition that is adapted for administration to an animal, typically oral administration of a human being.

The pharmaceutical composition according to the invention comprises a pharmaceutical excipient, preferably first pharmaceutical excipient, more preferably polyalkylene glycol, and a pharmaceutical component, preferably second pharmaceutical excipient, more preferably α-tocopherol.

For the purpose of the specification the term "pharmaceutical component" encompasses both, pharmacologically active substances (drugs) as well as pharmaceutical excipients. Thus, preferably, the pharmaceutical component is selected from pharmacologically active substances and pharmaceutical excipients.

Pharmaceutical excipients are known to the skilled person (cf. e.g. R. C. Rowe et al., Handbook of Pharmaceutical Excipients, Pharmaceutical Press; 6th edition 2009; E.-M. Hoepfner et al., Fiedler—Encyclopedia of Excipients, Editio Cantor, 6th edition 2008).

For the purpose of the specification, a "pharmaceutical excipient" is preferably to be regarded as any pharmacologically inactive substance typically used as a carrier for the active ingredients of a medication. The pharmaceutical excipient may have a physiological effect, e.g. like a vitamin, but not a pharmacological effect, like a drug. Typical examples of pharmaceutical excipients include antiadherents, binders, coating materials, disintegrants, fillers, diluents, flavours, colorants, glidants, lubricants, preservatives, sorbents, sweeteners, and the like. Any of the foregoing excipients can be divided into sub-groups. For example, preservatives can be divided into antioxidants, buffers, antimicrobial substances and the like; whereas binders can be divided into solution binders and dry binders. Several excipients simultaneously exhibit different properties so that they can serve different purposes. For example, polyethylene glycol can be used as binder, plasticizer and the like.

Pharmacologically active substances are also known to the skilled person. In this regard, it can be referred to e.g. the Anatomical Therapeutic Chemical (ATC) classification system of the WHO.

In a preferred embodiment, the pharmaceutical component is a pharmacologically active substance (drug). Under these circumstances, the pharmaceutical composition according to the invention comprises the pharmacologically active substance already.

In another preferred embodiment, the pharmaceutical component is a second pharmaceutical excipient. Under these circumstances, the pharmaceutical composition according to the invention comprises at least two pharmaceutical excipients, namely the above pharmaceutical excipient (=first pharmaceutical excipient) and the pharmaceutical component (=second pharmaceutical excipient).

When the pharmaceutical component is a pharmacologically active substance, this is preferably selected from the group consisting of hormones and related compounds, such as estrogens, gestagens, androgens, anti-estrogens, anti-gestagens, anti-androgens; and analgesics, such as opioids, preferably selected from the group consisting of tramadol, tapentadol, oxycodone, oxymorphone, hydrocodone, hydromorphone, morphin; and the physiologically acceptable salts thereof.

When the pharmaceutical component is a second pharmaceutical excipient, the pharmaceutical composition according to the invention does not necessarily have to comprise a pharmacologically active substance (drug). Rather, the pharmaceutical composition may exclusively consist of two or more pharmaceutical excipients. Under these circumstances, the pharmaceutical composition is preferably adapted for being further processed into a pharmaceutical dosage form by addition of a pharmacologically active substance and optionally, further pharmaceutical excipients. Thus, in a preferred embodiment, the pharmaceutical composition can be regarded as an intermediate in the preparation of a pharmaceutical dosage form, which intermediate as such does not yet contain the pharmacologically active substance of the pharmaceutical dosage form.

When the mixture comprises a third constituent beside the pharmaceutical excipient and the pharmaceutical component, said third constituent is preferably an additional pharmaceutical excipient, more preferably a polymer, still more preferably a polyalkylene oxide, yet more preferably a polyethylene oxide having a weight average molecular weight of at least 1 Mio g/mol, most preferably a polyethylene oxide having a weight average molecular weight of at least 4 Mio g/mol. It has been surprisingly found that the presence of the third constituent can improve the properties of the powdery pharmaceutical composition such as free-flowing properties, suppression of adherence, and the like. In particular, the presence of the third constituent can cause the pharmaceutical composition to fall apart in form of a free-flowing powder when exiting the extruder without a pronounced tendency of the powder particles to adhere to one another and to form aggregates or flocs, respectively.

In a preferred embodiment, the pharmaceutical composition essentially consists of a pharmaceutical excipient, preferably first pharmaceutical excipient, more preferably polyalkylene glycol, and a pharmaceutical component, preferably second pharmaceutical excipient, more preferably α-tocopherol, but does not contain any further ingredients, i.e. neither further pharmaceutical excipients nor pharmacologically active substances. In another preferred embodiment, the pharmaceutical composition essentially consists of a pharmaceutical excipient, preferably first pharmaceutical excipient, more preferably polyalkylene glycol, a pharmaceutical component, preferably second pharmaceutical excipient, more preferably α-tocopherol, and a third constituent, preferably an additional pharmaceutical excipient, more preferably a polymer, still more preferably a polyethylene oxide, but does not contain any further ingredients, i.e. neither further pharmaceutical excipients nor pharmacologically active substances.

The pharmaceutical composition is powdery. A "powder" is typically defined as an assembly of dry particles dispersed in air. For the purpose of the specification, "powdery" preferably means that the pharmaceutical composition is a dry bulk solid consisting of a large number of fine or very fine particles that may flow freely when shaken or tilted, i.e. that are not cemented together. Preferably, the texture is smooth in touch. In a preferred embodiment, the powder is free-flowing. In another preferred embodiment, however, the term "powdery" according to the invention also encompasses a multitude of relatively large particles, i.e. any particulate material, such as a multitude of particles having an average diameter of about 2 cm.

The particle size (grain size) of the powder is not limited. In a preferred embodiment, at least 90 wt.-% of the powder that has exited the extruder passes sieve size 4.75 mm, 3.35 mm, 2.81 mm, 2.38 mm, or 2.00 mm; more preferably 1.68 mm, 1.40 mm, 1.20 mm, 1.00 mm, or 0.853 mm; still more preferably 0.710 mm, 0.599 mm, 0.500 mm, 0.422 mm, or 0.354 mm; yet more preferably 0.297 mm, 0.251 mm, 0.211 mm, 0.178 mm, or 0.152 mm; most preferably 0.125 mm, 0.104 mm, 0.089 mm, 0.075 mm, or 0.066 mm; an in particular 0.053 mm, 0.044 mm, or 0.037 mm.

In a preferred embodiment, the powder is free flowing and preferably, has an average particle size of at most 100 μm, more preferably at most 90 μm, still more preferably at most 80 μm, yet more preferably at most 70 μm, most preferably at most 60 μm and in particular at most 50 μm. Method to determine the average particle size of powders are known to the skilled person. A suitable method is for example laser light scattering or sieve analysis.

According to the invention it is not required but possible that the powder which has exited the extruder is further grinded so that the particle size and particle size distribution of the final powdery pharmaceutical composition does not correspond to the particle size and particle size distribution of the powder that has exited the extruder.

The particle size (grain size) of the powdery pharmaceutical composition is not limited either. In a preferred embodiment, at least 90 wt.-% of the powdery pharmaceutical composition passes sieve size 4.75 mm, 3.35 mm, 2.81 mm, 2.38 mm, or 2.00 mm; more preferably 1.68 mm, 1.40 mm, 1.20 mm, 1.00 mm, or 0.853 mm; still more preferably 0.710 mm, 0.599 mm, 0.500 mm, 0.422 mm, or 0.354 mm; yet more preferably 0.297 mm, 0.251 mm, 0.211 mm, 0.178 mm, or 0.152 mm; most preferably 0.125 mm, 0.104 mm, 0.089 mm, 0.075 mm, or 0.066 mm; an in particular 0.053 mm, 0.044 mm, or 0.037 mm. In a particularly preferred embodiment, at least 90 wt.-% of the powdery pharmaceutical composition passes sieve size 1.00 mm, 0.95 mm, 0.90 mm or 0.85 mm.

In step (b) of the method according to the invention, a mixture of the pharmaceutical excipient, preferably first pharmaceutical excipient, more preferably polyalkylene glycol, and the pharmaceutical component, preferably second pharmaceutical excipient, more preferably α-tocopherol, optionally together with a third constituent, preferably another pharmaceutical excipient, is extruded.

Typically, extrusion is regarded as a process used to create objects of a fixed cross-sectional profile. A material is pushed or drawn through a die of the desired cross-section. Two main advantages of this process over other manufacturing processes is its ability to create very complex cross-sections and work materials that are brittle, because the material only encounters compressive and shear stresses. It also forms finished parts with an excellent surface finish.

For the purpose of the invention, however, extrusion is performed in an unusual fashion, namely so that the product, i.e. the extrudate, is a powder. This can be achieved by carefully adapting the extrusion parameters, e.g. screw geometry, extrusion temperature, screw speed, throughput, pressure and the like. Preferably, the extruder is not equipped with an extrusion die so that the pressure exerted to the mixture within the extruder is comparatively low. Preferably, the extruder is equipped neither with extrusion die nor with an adapter (e.g. Y-pipe).

For the purpose of the specification the term "extrudate" refers to any material exiting the extruder, e.g. an extruded strand or a powder.

Preferably, the pressure just ahead of the exit (outlet orifice) of the extruder does not exceed 25 bar or 20 bar, more preferably 15 bar or 10 bar, still more preferably 8.0 bar or 6.0 bar, yet more preferably 5.0 bar or 4.0 bar, most preferably 3.0 bar or 2.0 bar, and in particular 1.5 bar or 1.0 bar. The pressure just ahead of the exit of the extruder can be measured by conventional means and many commercialized extruders are already equipped with a respective manometer at the proper position. In a preferred embodiment, however, no pressure can be measured at all and the extrusion is performed under conditions imparting as minimal pressure as possible, preferably at most 1.0 bar, more preferably at most 0.8 bar, still more preferably at most 0.6 bar, yet more preferably at most 0.4 bar, most preferably at most 0.2 bar, and in particular at most 0.1 bar.

Preferably, the design of the screw elements and the extrusion conditions are adjusted to ensure that the extruded mass, in particular after its congealing, is not compacted or, if compaction cannot be completely avoided, the degree of compaction is as low as possible. A skilled person knows how to adjust such mild extrusion conditions, e.g. by regulating the screw speed.

Preferably, the extruder has an inner diameter of 10 mm to 100 mm, more preferably 12 mm to 90 mm, still more preferably 14 mm to 80 mm, most preferably 15 mm to 70 mm and in particular 15 mm to 60 mm. In a preferred embodiment, the extruder has an inner diameter of 18±10 mm, more preferably 18±8 mm, still more preferably 18±6 mm, yet more preferably 18±4 mm, most preferably 18±2 mm, and in particular 18±1 mm. In another preferred embodiment, the extruder has an inner diameter of 27±10 mm, more preferably 27±8 mm, still more preferably 27±6 mm, yet more preferably 27±4 mm, most preferably 27±2 mm, and in particular 27±1 mm. In yet another preferred embodiment, the extruder has an inner diameter of 50±10 mm, more preferably 50±8 mm, still more preferably 50±6 mm, yet more preferably 50±4 mm, most preferably 50±2 mm, and in particular 50±1 mm.

Preferably, the extruder has a length of 30 cm to 250 cm, more preferably 40 cm to 240 cm, still more preferably 50 cm to 230 cm, most preferably 60 cm to 220 cm and in particular 70 cm to 210 cm.

In a preferred embodiment, the ratio of extruder length in mm and extruder diameter in mm is within the range of 25±15, more preferably 25±10, still more preferably 25±8, yet more preferably 25±6, most preferably 25±4, and in particular 25±2.

In another preferred embodiment, the ratio of extruder length in mm and extruder diameter in mm is within the range of 30±15, more preferably 30±10, still more preferably 30±8, yet more preferably 30±6, most preferably 30±4, and in particular 30±2.

In still another preferred embodiment, the ratio of extruder length in mm and extruder diameter in mm is within the range of 40±15, more preferably 40±10, still more preferably 40±8, yet more preferably 40±6, most preferably 40±4, and in particular 40±2.

Preferably, the screw geometry is adapted so that the congealed material within the extruder is exerted a sufficient impact in order to yield a powdery pharmaceutical composition exiting the extruder. Thus, the extrusion parameters of the method according to the invention are preferably in contrast to the extrusion parameters of conventional methods where it is generally desired to manufacture a non-powdery extrusion strand having a smooth and excellent surface finish.

Typically, the screw geometry may be modified by varying the screw elements from which the screw is assembled. Conventional screw extruders are typically equipped with an extrusion axis adapted to carry a number of screw elements. Depending upon the extruder design and the design of the individual screw elements, the extrusion axis may carry about 10 to about 50 or more identical or different screw elements. In twin screw extruders (counter-rotating or co-rotating) the design of the individual screw elements must be such that contra-rotation or co-rotation about the two parallel extrusion axes is possible.

Preferably, each screw is equipped with (assembled from) at least 5, more preferably at least 10, most preferably 15 and in particular at least 20 identical or different screw elements.

The manufactures of screw extruders usually commercialize quite a number of different extrusion elements that can be employed in their extruders depending upon the individual demands of the extrusion technique. Examples of commercially available screw elements include screw transport elements, kneading elements, blank elements and the like. A skilled person is aware of typical screw elements.

Each screw element serves a particular purpose and a skilled person knows what screw element to choose in order to serve a particular purpose.

For example, a main purpose of screw transport elements is to effect transportation of the extruded material within the extruder from the inlet to the outlet and optionally, to impart the necessary pressure in front of the extrusion die. Screw transport elements can typically be divided in sub-types differing in their number of windings (threads) per standard length. For example, a screw transport element having two windings (threads) along a length of e.g. 100 mm differs from a screw transport element having three windings (threads) along the same length.

In contrast, a main purpose of kneading elements is to effect a vigorous mixing of the constituents of the extruded material without any substantial transportation. Kneading elements can typically also be divided in sub-types differing in their design and relative angle of kneaders. For example, a kneading element having two consecutive kneaders that are off-set 90° about the extrusion axis differs from a kneading element having two consecutive kneaders that are off-set 60° about the extrusion axis.

The design of the extrusion screws in the method according to the invention is not particularly limited. Preferably, however, each extrusion screw is equipped with (assembled from) a plurality of screw elements. Preferably, each extrusion screw comprises at least two different types of screw elements, more preferably at least three different types, still more preferably at least four different types, whereas every type of screw element may be represented by a single or a plurality of screw elements (i.e., of the same type). Screw elements of the same type may be located next to one another or in alternating, regular or irregular order and sequence with screw elements of other type(s), respectively.

FIG. 1 A is a schematic illustration of a screw transport element having two windings (threads) along its length (pitch). FIG. 1 B is a schematic illustration of a screw transport element having two windings (threads) along its length (pitch). FIG. 1 C is a schematic illustration of a screw transport element having three windings (threads) along its length (pitch). The length of the screw transport elements depicted in FIGS. 1 A to 1 C is identical.

Figure 2:
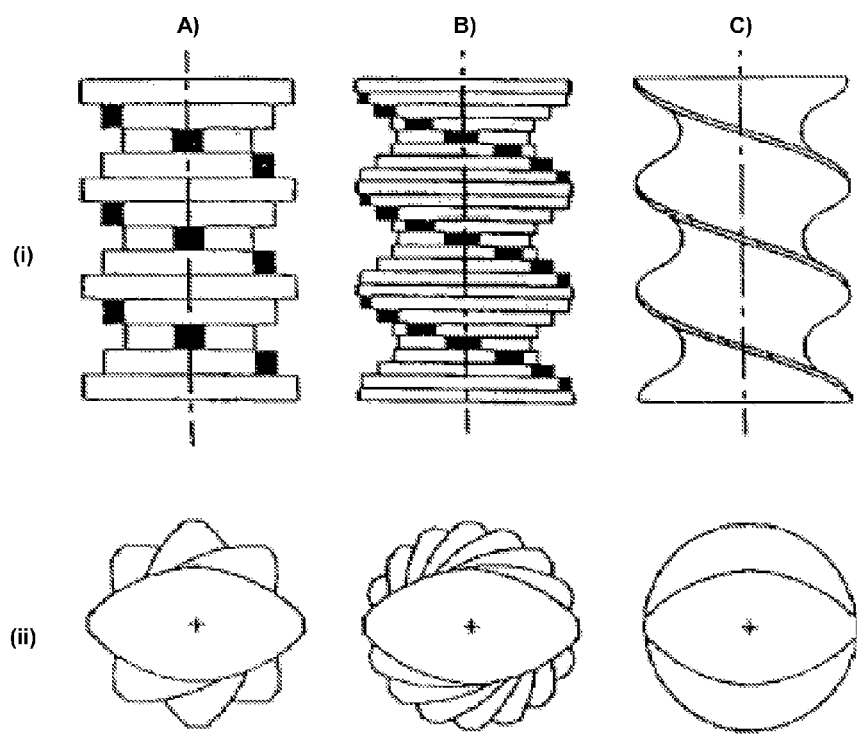

FIG. 2 shows different screw elements A), B) and C) in lengthwise (i) and cross-sectional (ii) views. These screws are suitable for co-rotating twin-screw extruders. A) is a square pitch bilobe screw, B) a screw having the same pitch with D/16 thick paddles at 22.5° offset and C) is a screw also having the same pitch with D/8 thick paddles at 45° offset.

Figure 3:
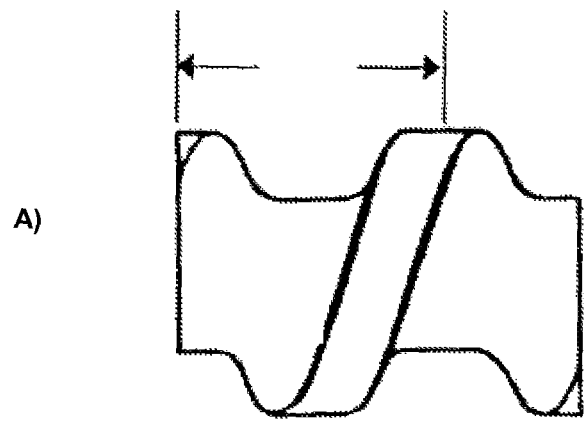
Figure 3:
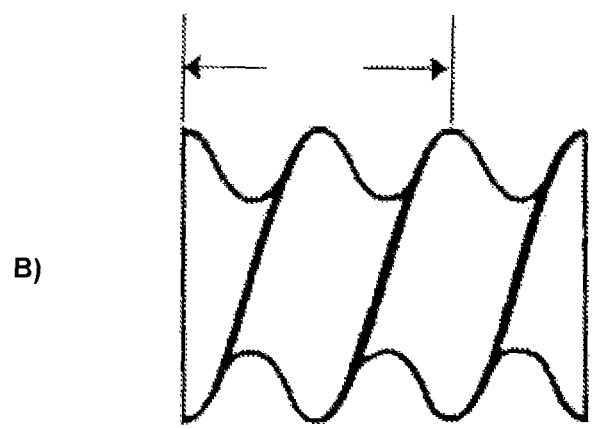
Figure 3:
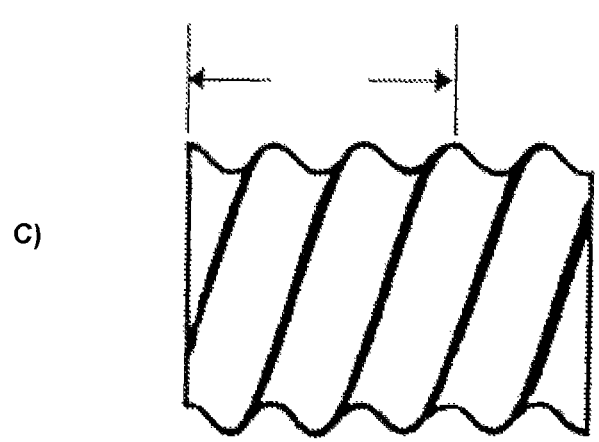

FIG. 3 shows different screw designs A), B) and C), where the pitch is defined as the axial distance for one revolution of screw flight expressed as absolute distance (mm), as ratio to screw diameter (D) or as flight helix angle (degrees).

In a preferred embodiment, each extrusion screw comprises at least having one screw element with a pitch (axial distance for one revolution of screw flight expressed as ratio to screw diameter (D)) within the range of 1.25±1.0 D, more preferably 1.25±0.75 D, still more preferably 0.5±0.4 D, 1.0±0.5 D or 1.75±0.5 D, yet more preferably 0.5±0.3 D, 1.0±0.4 D or 1.75±0.4 D, and most preferably 0.5±0.25 D, 1.0±0.25 D or 1.75±0.25 D.

Figure 4:
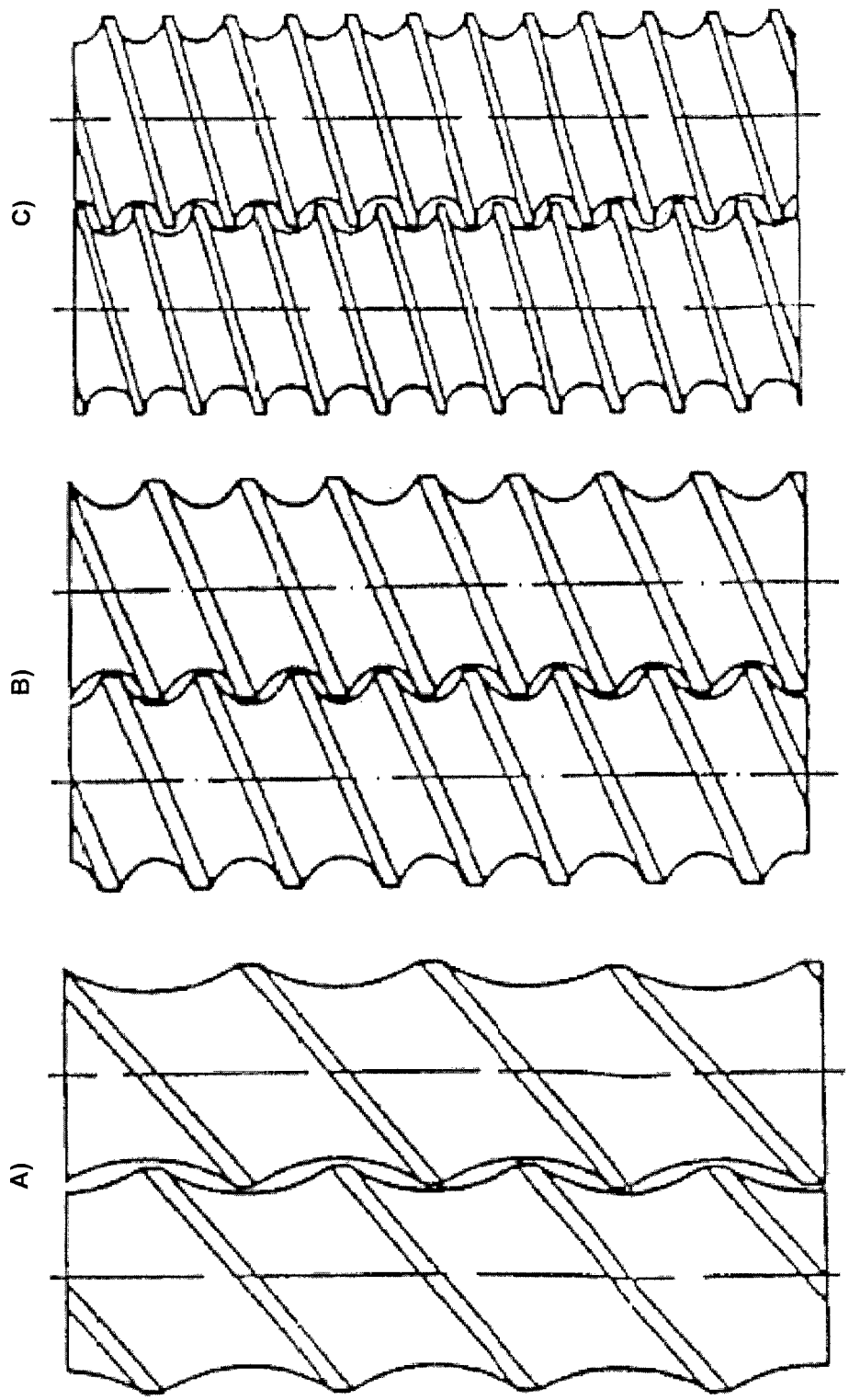

FIG. 4 shows two parallel screws of different screw designs A), B) and C) differing in their pitch. FIG. 4 A) shows a high screw pitch ($\approx$1.5 D to 2 D), FIG. 4 B) shows a medium screw pitch ($\approx$1 D) and FIG. 4 C) shows a low screw pitch ($\approx$0.25 D to 0.75 D). High screw pitch has the largest volumetric displacement, the fastest conveying speed, the lowest degree-of-fill and feeding, venting. Medium screw pitch has an intermediate volumetric displacement and moderate conveying speed. It increases the degree-of-fill downstream of high pitch screws and causes compression after feeding. Melt conveying is intermediate. Low screw pitch has the lowest volumetric displacement and the slowest conveying speed. It increases the degree-of-fill downstream of medium pitch screws. It may cause a maximum degree-of-fill without downstream pressure, heat transfer, pumping.

Figure 5:
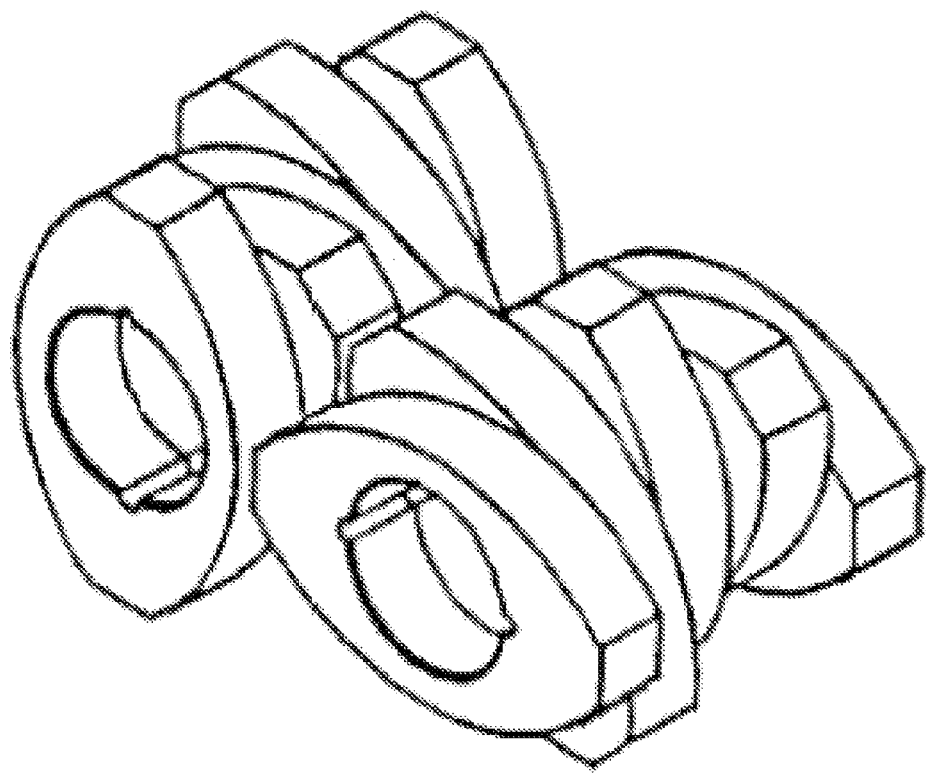

FIG. 5 shows a typical kneading element (mixing element) in perspective view. Kneading elements are typically characterized by their direction of conveying, the stagger offset angle, the kneading disc width, the number of kneading discs and the number of flights.

In a preferred embodiment of the method according to the invention, each extrusion screw is equipped with (assembled from) at least two different types of screw transport elements differing, optionally inter alia, in their number of windings (threads) per standard length, whereas in at least a portion of the extrusion screw the type of screw transport elements having the lower number of windings (threads) is located upstream with respect to the screw transport elements having the higher number of windings (threads).

In another preferred embodiment of the method according to the invention, each extrusion screw is equipped with (assembled from) at least two different types of screw transport elements differing, optionally inter alia, in their chamber volume per standard length, whereas in at least a portion of the extrusion screw the type of screw transport elements having the smaller chamber volume is located upstream with respect to the screw transport elements having the larger chamber volume. For the purpose of the specification, the chamber volume is to be regarded as the space between the screw elements and the extruder wall, i.e. the inner hollow space that guides the extruded mass through the extruder.

Preferably, each extrusion screw is equipped with (assembled from) at least two different types of screw transport elements (a) and (b), whereas each type of screw transport element is represented by one or more individuals. In a preferred embodiment, the number of windings (threads) per standard length of elements (b) exceeds the number of windings (threads) of elements (a). In another preferred embodiment, the chamber volume per standard length of elements (b) exceeds the chamber volume of elements (a). In still another preferred embodiment, the pitch of elements (b) exceeds the pitch of elements (a). In yet another preferred embodiment, the conveying speed of elements (b) exceeds the conveying speed of elements (a). In another preferred embodiment, the volumetric displacement of elements (b) exceeds the volumetric displacement of elements (a). Preferably, a sequence of four consecutive elements that are independently chosen from screw transport elements of type (a) and screw transport elements of type (b) forms a portion of the extrusion screw. Preferred embodiments $A^1$ to $A^{14}$ of how these screw elements are positioned along the extrusion axis of said portion from an upstream location to a downstream location are summarized in the table here below:

| | upstream -> downstream | | | |
|---|---|---|---|---|
| $A^1$ | (a) | (a) | (a) | (b) |
| $A^2$ | (a) | (a) | (b) | (a) |
| $A^3$ | (a) | (b) | (a) | (a) |
| $A^4$ | (b) | (a) | (a) | (a) |
| $A^5$ | (a) | (a) | (b) | (b) |
| $A^6$ | (a) | (b) | (a) | (b) |
| $A^7$ | (a) | (b) | (b) | (a) |
| $A^8$ | (b) | (a) | (a) | (b) |
| $A^9$ | (b) | (a) | (b) | (a) |
| $A^{10}$ | (b) | (b) | (a) | (a) |
| $A^{11}$ | (b) | (b) | (b) | (a) |
| $A^{12}$ | (b) | (b) | (a) | (b) |
| $A^{13}$ | (b) | (a) | (b) | (b) |
| $A^{14}$ | (a) | (b) | (b) | (b) |

In a preferred embodiment, the length of the extrusion screw corresponds to the length of the extruder so that the entire extrusion screw is mounted by the extruder block. In another preferred embodiment the length of the extrusion screw is such that it protrudes from the extruder block, typically by several cm, e.g. about 2.5, 5 or 7.5 cm.

The method according to the invention comprises the extrusion of a mixture of the pharmaceutical excipient and the pharmaceutical component in an extruder at a temperature profile allowing a liquid melt of the mixture to congeal in the extruder and to exit the extruder in form of a powder. Thus, when the extruder is a screw extruder, its extrusion axis or axes, respectively, comprise an upstream portion that serves the purpose of extruding the not yet congealed mixture and a downstream portion that serves the purpose of extruding the congealed mixture.

In a preferred embodiment of the method according to the invention, the screw elements forming said downstream portion of the extrusion screw comprise screw elements imparting a relatively high mechanical impact on the congealed mixture in order to yield a powdery pharmaceutical composition. Thus, as far as the design of the extrusion elements in this downstream portion is concerned, extrusion conditions are comparatively harsh.

Preferably, parallel to the temperature profile in the extruder that allows the liquid melt of the mixture to congeal in the extruder and to exit the extruder in form of a powder, there is an extrusion screw profile increasing the mechanical impact exerted by the extrusion elements further supporting that the extruded material exits the extruder in form of a powder.

The extruder is preferably equipped with at least two heating elements that can be adjusted to different temperatures independently. Preferably, the extruder comprises at least three, more preferably at least four, still more preferably at least five, yet more preferably at least six, most preferably at least seven and in particular at least eight of such heating elements adjustable to different temperatures independently.

These heating elements allow adjusting the desired temperature profile within the extruder.

Preferably, the extruder is equipped with at least four consecutive heating elements $H_1$, $H_2$, $H_3$ and $H_4$ which are set at the corresponding temperatures $T_1$, $T_2$, $T_3$ and $T_4$, respectively. $H_1$ is located upstream with respect to $H_2$ to $H_4$, $H_2$ is located upstream with respect to $H_3$ and $H_4$ and $H_3$ is located upstream with respect to $H_4$. Preferred embodiments of the relationship $T_1$ to $T_4$ are summarized here below:
$T_1=T_2=T_3=T_4$; $T_1>T_2=T_3=T_4$; $T_1=T_2>T_3=T_4$;
$T_1=T_2=T_3>T_4$; $T_1<T_2=T_3=T_4$, $T_1=T_2<T_3=T_4$;
$T_1=T_2=T_3<T_4$; $T_1>T_2>T_3=T_4$; $T_1>T_2=T_3>T_4$;
$T_1=T_2>T_3>T_4$; $T_1<T_2<T_3=T_4$; $T_1<T_2=T_3<T_4$;
$T_1=T_2<T_3<T_4$; $T_1>T_2>T_3>T_4$; or $T_1<T_2<T_3<T_4$.

Preferably, in step (b) of the method according to the invention, extrusion is performed by means of a screw extruder, preferably a twin screw extruder having contra-rotating or co-rotating screws. It is also possible to perform extrusion by means of a planetary gear extruder (planetary roller extruder). Suitable extruders are known to the skilled person and commercially available. A suitable twin screw extruder is for example commercialized by Leistritz, type ZSE 18PH 40 D.

A skilled person recognizes, however, that the gist of the method according to the invention can also be realized by equivalent means typically employed in order to process viscous or highly viscous masses, wherein processing typically involves heating, mixing, cooling, shearing, and/or the like. Exemplified means include roll coolers or barrel coolers, cool belts, granulators, coaters, etc.

In the course of the extrusion process, the extruded material is typically transported along the longitudinal axis of the extruder from the inlet (feeding point) to the outlet (exit). Material movement is typically effected by the rotation of the screws and by the new starting material entering the inlet of the extruder. For the purpose of the specification, two locations along the longitudinal axis of the extruder may be qualified as "upstream" and "downstream" with respect to the direction of extrusion. The location upstream is closer to the inlet of the extruder than the location downstream and vice versa, the location downstream is closer to the exit of the extruder than the location upstream.

The temperature profile within the extruder is adjusted to ensure that a liquid melt of the mixture is allowed to congeal in the extruder before it exits the extruder. Thus, according to the method of the invention, at least at one upstream location within the extruder the pharmaceutical excipient, preferably first pharmaceutical excipient, more preferably polyalkylene glycol, and the pharmaceutical component, preferably second pharmaceutical excipient, more preferably α-tocopherol, optionally together with a third constituent, preferably another pharmaceutical excipient, are present in the molten state. Melting is typically achieved by adjusting the temperature profile so that at said upstream location the temperature of the mixture (extruded material) is sufficiently high.

This does not necessarily mean that the temperature of the mixture (extruded material) in the extruder at said one upstream location must be above the melting points/ranges of both, the pharmaceutical excipient, preferably first pharmaceutical excipient, more preferably polyalkylene glycol, and the pharmaceutical component, preferably second pharmaceutical excipient, more preferably α-tocopherol, and the optionally present third constituent, preferably another pharmaceutical excipient. Depending upon the nature and the amount of the excipients it may be sufficient that the temperature is above the melting point/range of just one of the two or three ingredients so that it forms a liquid melt in which the other is (are) dissolved.

Preferably, however, the temperature of the mixture (extruded material) in the extruder at said one upstream location is above the melting points/ranges of both, the pharmaceutical excipient, preferably first pharmaceutical excipient, more preferably polyalkylene glycol, and the pharmaceutical component, preferably second pharmaceutical excipient, more preferably α-tocopherol, and the optionally present third constituent.

The liquid melt may be formed, i.e. generated, within the extruder by initially heating the mixture (extruded material) having a temperature below its melting point/range to a temperature above its melting point/range so that a liquid melt is formed. Alternatively, however, the liquid melt may already be fed into the extruder, i.e. the liquid melt of the pharmaceutical excipient, preferably first pharmaceutical excipient, more preferably polyalkylene glycol, and the pharmaceutical component, preferably second pharmaceutical excipient, more preferably α-tocopherol, optionally together with a third constituent, preferably another pharmaceutical excipient, may be formed outside the extruder and then be supplied to the inlet of the extruder so that the starting material enters the extruder already in molten liquid state. Preferably, said liquid state is maintained for a while in the course of the extrusion process.

In the course of the extrusion process and as a consequence of the temperature profile, the liquid melt is allowed to congeal in the extruder. The liquid melt congeals, i.e. solidifies to a solid material by cooling. Thus, according to the method of the invention, at least at one downstream location within the extruder the pharmaceutical excipient, preferably first pharmaceutical excipient, more preferably polyalkylene glycol, and the pharmaceutical component, preferably second pharmaceutical excipient, more preferably α-tocopherol, optionally together with a third constituent, preferably another pharmaceutical excipient, are present in the congealed, i.e. solidified state. Congealing is typically achieved by adjusting the temperature profile so that at said downstream location the temperature of the mixture (extruded material) is sufficiently low.

This does not necessarily mean that the temperature of the mixture (extruded material) in the extruder at said one downstream location must be below the melting points/ranges of both, the pharmaceutical excipient, preferably first pharmaceutical excipient, more preferably polyalkylene glycol, and the pharmaceutical component, preferably second pharmaceutical excipient, more preferably α-tocopherol, and the optionally present third constituent. Depending upon the nature and the amount of the excipients it may be sufficient that the temperature is below the melting point/range of just one of the two ingredients so that it solidifies with the other ingredient being dissolved in it.

Preferably, when the congealed mixture exits the extruder, it has a temperature of at least 5° C., preferably at least 10° C., more preferably at least 15° C., still more preferably at least 20° C., yet more preferably at least 25° C., most preferably at least 30° C. and in particular at least 35° C., below the melting point/temperature of the pharmaceutical excipient, preferably first pharmaceutical excipient, more preferably polyalkylene glycol, and/or the pharmaceutical component, preferably second pharmaceutical excipient, more preferably α-tocopherol and/or the optionally present third constituent.

In a preferred embodiment of the method according to the invention, in step (b) the temperature profile comprises a temperature gradient of temperature $T_1$ to temperature $T_2$, where $T_1 > T_2$ and where $T_1$ is above the melting point/range of the pharmaceutical excipient, preferably first pharmaceutical excipient, more preferably polyalkylene glycol, and/or the pharmaceutical component, preferably second pharmaceutical excipient, more preferably α-tocopherol and/or the optionally present third constituent; and/or $T_2$ is below the melting point/range of the pharmaceutical excipient, preferably first pharmaceutical excipient, more preferably polyalkylene glycol and/or pharmaceutical component, preferably second pharmaceutical excipient, more preferably α-tocopherol, and/or the optionally present third constituent.

$T_1$ and $T_2$ are preferably adjusted be means of the heating elements of the extruder. Preferably $T_1$ and $T_2$ correspond to the temperatures at which the heating elements are heated. Preferably, $T_1$ is within the range of from 25° C. to 115° C., or 30° C. to 110° C., more preferably 35° C. to 105° C., or 40° C. to 100° C., still more preferably 45° C. to 95° C., or 50° C. to 90° C., yet more preferably 55° C. to 85° C., most preferably 60° C. to 80° C., and in particular 65° C. to 75° C.; and/or $T_2$ is within the range of from −20° C. to 50° C., more preferably −10° C. to 40° C., still more preferably −5° C. to 35° C., yet more preferably 0° C. to 30° C., most preferably 5° C. to 25° C., and in particular 10° C. to 20° C.

In a preferred embodiment, $T_1$ is at least 0.5° C. or at least 1.0° C., more preferably at least 1.5° C. or at least 2.0° C., still more preferably at least 2.5° C. or at least 3.0° C., yet more preferably at least 3.5° C. or at least 4.0° C., most preferably at least 4.5° C. or at least 5.0° C., and in particular at least 5.5° C. or at least 6.0° C. above the melting point of the pharmaceutical excipient, preferably first pharmaceutical excipient, more preferably polyalkylene glycol, and/or the pharmaceutical component, preferably second pharmaceutical excipient, more preferably α-tocopherol and/or the optionally present third constituent.

In another preferred embodiment, $T_1$ is at least 5° C. or at least 10° C., more preferably at least 15° C. or at least 20° C., still more preferably at least 25° C. or at least 30° C., yet more preferably at least 35° C. or at least 40° C., most preferably at least 45° C. or at least 50° C., and in particular at least 55° C. or at least 60° C. above the melting point of the pharmaceutical excipient, preferably first pharmaceutical excipient, more preferably polyalkylene glycol, and/or the pharmaceutical component, preferably second pharmaceutical excipient, more preferably α-tocopherol and/or the optionally present third constituent.

In a preferred embodiment, $T_2$ is at least 1.0° C. or at least 2.0° C., more preferably at least 3.0° C. or at least 4.0° C., still more preferably at least 5.0° C. or at least 6.0° C., yet more preferably at least 7.0° C. or at least 8.0° C., most preferably at least 9.0° C. or at least 10° C., and in particular at least 11° C. or at least 12° C. above the melting point of the pharmaceutical excipient, preferably first pharmaceutical excipient, more preferably polyalkylene glycol, and/or the pharmaceutical component, preferably second pharmaceutical excipient, more preferably α-tocopherol and/or the optionally present third constituent.

In another preferred embodiment, $T_2$ is at least 2.5° C. or at least 5.0° C., more preferably at least 7.5° C. or at least 10° C., still more preferably at least 12.5° C. or at least 15° C., yet more preferably at least 17.5° C. or at least 20° C., most preferably at least 25° C. or at least 30° C., and in particular at least 35° C. or at least 40° C. below the melting point of the pharmaceutical excipient, preferably first pharmaceutical excipient, more preferably polyalkylene glycol, and/or the pharmaceutical component, preferably second pharmaceutical excipient, more preferably α-tocopherol and/or the optionally present third constituent.

In a preferred embodiment, the pharmaceutical excipient, preferably first pharmaceutical excipient, more preferably polyalkylene glycol, and the pharmaceutical component, preferably second pharmaceutical excipient, more preferably α-tocopherol, and the optionally present third constituent, are fed into the extruder in form of a liquid melt having a sufficiently high temperature, preferably within the range of $T_1 \pm 10°$ C., more preferably $T_1 \pm 8.0°$ C., still more preferably $T_1 \pm 6.0°$ C., yet more preferably $T_1 \pm 4.0°$ C., most preferably $T_1 \pm 2.0°$ C., and in particular $T_1 \pm 1.0°$ C.

The congealed mixture then exits the extruder in form of a powder. This means that in the extruder the liquid melt does not only congeal into a solid material but is further comminuted into a powder, at least to a certain extent.

It has been surprisingly found that the mechanical impact, in particular the shear forces within the extruder are sufficient in order to directly prepare a powder in one step. This has the advantage that subsequent grinding steps are facilitated, if any, or can even be completely omitted. This is a substantial advantage, as grinding causes heating which in turn may cause the ground material to become sticky.

Thus, in a preferred embodiment of the method according to the invention, the material exiting the extruder is not subjected to any further steps, particularly to no grinding, such that the material exiting the extruder is the powdery pharmaceutical composition according to the invention.

In a preferred embodiment, the method according to the invention comprises the preceding step of (a) mixing the pharmaceutical excipient, preferably first pharmaceutical excipient, more preferably polyalkylene glycol, with the pharmaceutical component, preferably second pharmaceutical excipient, more preferably α-tocopherol, and the optionally present third constituent, outside the extruder and then feeding the resultant mixture into the extruder; or feeding the pharmaceutical excipient, preferably first pharmaceutical excipient, more preferably polyalkylene glycol, and the pharmaceutical component, preferably second pharmaceutical excipient, more preferably α-tocopherol, and the optionally present third constituent, into the extruder at different feeding points, where the feeding point for the pharmaceutical excipient, preferably first pharmaceutical excipient, more preferably polyalkylene glycol, is located upstream with respect to the feeding point for the pharmaceutical component, preferably second pharmaceutical excipient, more preferably α-tocopherol, or vice versa.

Step (a) precedes step (b), i.e. step (b) is performed after step (a) has been completed.

Preferably, in step (a) the pharmaceutical component, preferably second pharmaceutical excipient, more preferably α-tocopherol, is dissolved in the molten pharmaceutical excipient, preferably first pharmaceutical excipient, more preferably polyalkylene glycol and/or the optionally present third constituent, or vice versa.

In another preferred embodiment, the method according to the invention comprises the subsequent step(s) of
(c) grinding the powder; and
(d) optionally, grading the powder.

Grinding may be achieved by conventional grinding equipment.

Typically, the method according to the invention does not comprise any spray congealing or spray drying step. It has been surprisingly found that by the method according to the invention laborious steps that require sophisticated equipment and process control can be omitted without deteriorating product quality. Thus, in a particularly preferred embodiment, besides extrusion, the method according to the invention does not comprise any separate grinding, spray congealing or spray drying steps.

In a preferred embodiment, the powder is a homogeneous mixture of the pharmaceutical excipient, preferably first pharmaceutical excipient, more preferably polyalkylene glycol, and the pharmaceutical component, preferably second pharmaceutical excipient, more preferably α-tocopherol and the optionally present third constituent. For the purpose of the specification, "homogeneous" preferably means that the standard deviation (SD) as a measure of blend uniformity (BU) of the powder is at most 5.0 SD %, more preferably at most 4.5 SD %, still more preferably at most 4.0 SD %, yet more preferably at most 3.5 SD %, most preferably at most 3.0 SD % and in particular at most 2.5 SD %. Methods to determine blend uniformity of powders are known to the skilled person. For example, a suitable method is near infrared spectroscopy (NIR), other methods are described in the Eur. Ph.

The pharmaceutical excipient and the pharmaceutical component are not particularly limited.

Preferably, the pharmaceutical excipient, preferably first pharmaceutical excipient, is hydrophilic and the pharmaceutical component, preferably second pharmaceutical excipient, is hydrophobic, or vice versa. When the pharmaceutical composition comprises a third constituent, this is preferably hydrophilic as well.

A skilled person knows how to distinguish hydrophobic substances from hydrophilic substances. For the purpose of the specification, hydrophilic substances preferably have a solubility in pure water at 20° C. of at least 10 g/l, more preferably at least 50 g/l, still more preferably at least 100 g/l, yet more preferably at least 200 g/l, most preferably at least 300 g/l and in particular at least 400 g/l. For the purpose of the specification, hydrophobic substances preferably have a solubility in pure water at 20° C. of at most 1 g/l, more preferably at most 0.5 g/l, still more preferably at most 1.0 g/l, yet more preferably at most 0.05 g/l, most preferably at most 0.01 g/l and in particular at most 0.005 g/l.

In a preferred embodiment, the pharmaceutical excipient, preferably first pharmaceutical excipient, has a melting point/range within the range of 60±30° C., more preferably 60±25° C., still more preferably 60±20° C., yet more preferably 60±15° C., most preferably 60±10° C., and in particular 60±5.0° C.

In a preferred embodiment, the pharmaceutical component, preferably second pharmaceutical excipient, has a melting point/range within the range of 2.0±30° C., more preferably 2.0±25° C., still more preferably 2.0±20° C., yet more preferably 2.0±15° C., most preferably 2.0±10° C., and in particular 2.0±5.0° C.

In a preferred embodiment, the pharmaceutical component, preferably second pharmaceutical excipient, has a density (at 20° C.) within the range of 0.950±0.040 g/cm$^3$, more preferably 0.950±0.030 g/cm$^3$, still more preferably 0.950±0.025 g/cm$^3$, yet more preferably 0.950±0.020 g/cm$^3$, most preferably 0.950±0.015 g/cm$^3$, and in particular 0.950±0.010 g/cm$^3$.

In a preferred embodiment,
the pharmaceutical excipient, preferably first pharmaceutical excipient, is a polymer, more preferably a linear polymer, still more preferably a water-soluble polymer, yet more preferably a polyalkylene glycol, most preferably a polyethylene glycol; and/or
the pharmaceutical component, preferably second pharmaceutical excipient, is an antioxidant, preferably a tocopherol component, more preferably α-tocopherol.

For the purpose of the specification, the term "polyalkylene glycol" comprises e.g. polyethylene glycol, polypropylene glycol, blends thereof and copolymers thereof.

For the purpose of the specification, "tocopherol component" refers to α-tocopherol (vitamin E) and its derivatives such as tocopherol acetate.

In a preferred embodiment, the pharmaceutical excipient, preferably first pharmaceutical excipient, is a polyalkylene glycol, preferably a polyethylene glycol, having a weight average molecular weight within the range of from 6,000±5,000 g/mol, more preferably 6,000±4,000 g/mol, still more preferably 6,000±3,000 g/mol, yet more preferably 6,000±2,000 g/mol, most preferably 6,000±1,500 g/mol, and in particular 6,000±1,000 g/mol.

Preferably, the pharmaceutical composition does not contain any pharmacologically active substance (besides the tocopherol component).

In a preferred embodiment, the relative weight ratio of the pharmaceutical excipient, preferably first pharmaceutical excipient, more preferably polyalkylene glycol, to the pharmaceutical component, preferably second pharmaceutical excipient, more preferably α-tocopherol, is within the range of from 1000:1 to 1:1, more preferably 900:1 to 5:1, still more preferably 800:1 to 10:1, yet more preferably 700:1 to 15:1, most preferably 600:1 to 20:1, and in particular 500:1 to 25:1.

In a preferred embodiment, the relative weight ratio of the pharmaceutical excipient, preferably first pharmaceutical excipient, more preferably polyalkylene glycol, to the pharmaceutical component, preferably second pharmaceutical excipient, more preferably α-tocopherol, is at most 1000:1, more preferably at most 900:1, still more preferably at most 800:1, yet more preferably at most 700:1, most preferably at most 600:1 and in particular at most 500:1.

In another preferred embodiment, the relative weight ratio of the pharmaceutical excipient, preferably first pharmaceutical excipient, more preferably polyalkylene glycol, to the pharmaceutical component, preferably second pharmaceutical excipient, more preferably α-tocopherol, is at least 1:1, more preferably at least 5:1, still more preferably at least 10:1, yet more preferably at least 20:1, most preferably at least 30:1 and in particular at least 50:1.

When the pharmaceutical composition comprises a third constituent, preferably another pharmaceutical excipient, the relative weight ratio of the pharmaceutical excipient, preferably first pharmaceutical excipient, more preferably polyalkylene glycol, to said third constituent, preferably another pharmaceutical excipient, preferably polyethylene oxide, is within the range of from 99:1 to 1:5, more preferably 50:1 to 1:4, still more preferably 30:1 to 1:3, yet more preferably 20:1 to 1:2, most preferably 15:1 to 1:1 and in particular 10:1 to 2:1.

Preferably, the content of the pharmaceutical excipient, preferably first pharmaceutical excipient, more preferably polyalkylene glycol, in the pharmaceutical composition is at least 50 wt.-% or at least 55 wt.-%, still more preferably at least 60 wt.-% or at least 65 wt.-%, yet more preferably at least 70 wt.-% or at least 75 wt.-%, most preferably at least 80 wt.-%, at least 82.5 wt.-%, at least 85 wt.-% or at least 87.5 wt.-%, and in particular at least 90 wt.-%, at least 91 wt.-%, at least 92 wt.-%, at least 93 wt.-%, at least 94 wt.-%, at least 95 wt.-%, at least 96 wt.-%, at least 97 wt.-%, at least 98 wt.-%, or at least 99 wt.-%, based on the total weight of the pharmaceutical composition.

Preferably, the content of the optionally present third constituent, preferably another pharmaceutical excipient, more preferably polyethylene oxide, in the pharmaceutical composition is at least 0.1 wt.-% or at least 0.2 wt.-%, still more preferably at least 0.5 wt.-% or at least 1.0 wt.-%, yet more preferably at least 2.0 wt.-% or at least 5.0 wt.-%, most preferably at least 7.5 wt.-%, at least 10 wt.-%, at least 12.5 wt.-% or at least 15 wt.-%, and in particular at least 20 wt.-%, at least 25 wt.-%, at least 30 wt.-%, at least 35 wt.-%, at least 40 wt.-%, at least 45 wt.-%, at least 50 wt.-%, at least 55 wt.-%, at least 60 wt.-%, or at least 65 wt.-%, based on the total weight of the pharmaceutical composition.

Preferably, the content of the pharmaceutical component, preferably second pharmaceutical excipient, more preferably α-tocopherol, in the pharmaceutical composition is at most 50 wt.-% or at most 45 wt.-%, more preferably at most 40 wt.-% or at most 35 wt.-%, still more preferably at most 30 wt.-% or at most 25 wt.-%, yet more preferably at most 20 wt.-%, at most 17.5 wt.-%, at most 15 wt.-% or at most 12.5 wt.-%, most preferably 10 wt.-%, at most 9.0 wt.-%, at most 8.0 wt.-%, at most 7.0 wt.-%, or at most 6.0 wt.-%, and in particular at most at most 5.0 wt.-%, at most 4.0 wt.-%, at most 3.0 wt.-%, at most 2.0 wt.-%, or at most 1.0 wt.-%, based on the total weight of the pharmaceutical composition.

In a preferred embodiment, the content of the pharmaceutical component, preferably pharmacologically active ingredient, is at most 10 wt.-% or at most 9.0 wt.-%, more preferably at most 8.0 wt.-% or at most 7.0 wt.-%, still more preferably at most 6.0 wt.-% or at most 5.0 wt.-%, yet more preferably at most 4.5 wt.-%, at most 4.0 wt.-%, at most 3.5 wt.-% or at most 3.0 wt.-%, most preferably 2.5 wt.-%, at most 2.0 wt.-%, at most 1.5 wt.-%, at most 1.0 wt.-%, or at most 0.75 wt.-%, and in particular at most at most 0.5 wt.-%, at most 0.25 wt.-%, at most 0.1 wt.-%, at most 0.05 wt.-%, at most 0.01 wt.-%, at most 0.005 wt.-% or at most 0.001 wt.-%, based on the total weight of the pharmaceutical composition.

In a preferred embodiment, the content of the pharmaceutical component, preferably second pharmaceutical excipient, more preferably α-tocopherol, in the pharmaceutical composition is within the range of 5.0±2.5 wt.-%, more preferably 5.0±2.0 wt.-%, still more preferably 5.0±1.5 wt.-%, yet more preferably 5.0±1.0 wt.-%, most preferably 5.0±0.5 wt.-%, and in particular 5.0±0.25 wt.-%, based on the total weight of the pharmaceutical composition.

In another preferred embodiment, the content of the pharmaceutical component, preferably second pharmaceutical excipient, more preferably α-tocopherol, in the pharmaceutical composition is within the range of 4.0±2.5 wt.-%, more preferably 4.0±2.0 wt.-%, still more preferably 4.0±1.5 wt.-%, yet more preferably 4.0±1.0 wt.-%, most preferably 4.0±0.5 wt.-%, and in particular 4.0±0.25 wt.-%, based on the total weight of the pharmaceutical composition.

In still another preferred embodiment, the content of the pharmaceutical component, preferably second pharmaceutical excipient, more preferably α-tocopherol, in the pharmaceutical composition is within the range of 3.0±2.5 wt.-%, more preferably 3.0±2.0 wt.-%, still more preferably 3.0±1.5 wt.-%, yet more preferably 3.0±1.0 wt.-%, most preferably 3.0±0.5 wt.-%, and in particular 3.0±0.25 wt.-%, based on the total weight of the pharmaceutical composition.

In yet another preferred embodiment, the content of the pharmaceutical component, preferably second pharmaceutical excipient, more preferably α-tocopherol, in the pharmaceutical composition is within the range of 2.0±1.5 wt.-%, more preferably 2.0±1.25 wt.-%, still more preferably 2.0±1.0 wt.-%, yet more preferably 2.0±0.75 wt.-%, most preferably 2.0±0.5 wt.-%, and in particular 2.0±0.25 wt.-%, based on the total weight of the pharmaceutical composition.

In another preferred embodiment, the content of the pharmaceutical component, preferably second pharmaceutical excipient, more preferably α-tocopherol, in the pharmaceutical composition is within the range of 1.0±0.8 wt.-%, more preferably 1.0±0.6 wt.-%, still more preferably 1.0±0.5 wt.-%, yet more preferably 1.0±0.4 wt.-%, most preferably 1.0±0.3 wt.-%, and in particular 1.0±0.2 wt.-%, based on the total weight of the pharmaceutical composition.

The method according to the invention can be performed batch-wise or continuously.

Preferably, the method is performed continuously and a mixture of the pharmaceutical excipient, preferably first pharmaceutical excipient, more preferably polyalkylene glycol, and the pharmaceutical component, preferably second pharmaceutical excipient, more preferably α-tocopherol, and the optionally present third constituent, is automatically dosed into the extruder, preferably in form of a melt. First preliminary tests revealed that continuous dosing can be realized by standard equipment.

A further aspect of the invention relates to a method for the manufacture of a pharmaceutical dosage form comprising the method according to the invention as described above. Preferably, the pharmaceutical dosage form has a breaking strength of at least 400 N, more preferably at least 500 N, still more preferably at least 600 N, yet more preferably at least 700 N, most preferably at least 800 N and in particular at least 900 N. Dosage forms exhibiting such a high breaking strength are known from the prior art. In this regard it can be referred to e.g. WO 2005/016313, WO 2005/016314, WO 2005/063214, WO 2005/102286, WO 2006/002883, WO 2006/002884, WO 2006/002886, WO 2006/082097, WO 2006/082099, WO 2008/107149 and WO2009/092601.

Preferably, the method for the manufacture of a pharmaceutical dosage form comprises the step of formulating the powdery pharmaceutical composition comprising the first pharmaceutical excipient and the second pharmaceutical excipient and the optionally present third constituent, as described above together with

- a pharmacologically active substance, preferably an opioid, and/or
- a high molecular weight polyalkylene oxide, preferably polyethylene oxide, preferably having a weight average molecular weight of a least 200,000 g/mol, more preferably at least 500,000 g/mol, still more preferably at least 750,000 g/mol, yet more preferably at least 1,000,000 g/mol and in particular within the range of from 1,000,000 g/mol to 10,000,000 g/mol; and/or
- a cellulose ether, preferably hydroxypropylmethyl cellulose or hydroxypropylcellulose.

Thus, in the method for the manufacture of a pharmaceutical dosage form according to the invention, the powdery pharmaceutical composition is preferably employed as intermediate.

Preferably, the powdery pharmaceutical composition does not substantially alter the release of the pharmacologically active substance from the pharmaceutical dosage form, i.e. the in vitro release profile of the pharmaceutical dosage form is not substantially influenced by the presence of the powdery pharmaceutical composition. In this regard, "substantially" preferably means 2%, more preferably 1%, i.e. the presence of the powdery pharmaceutical composition preferably does not alter the in vitro release profile by more than 2% compared to a dosage form not containing the powdery pharmaceutical composition.

In a preferred embodiment, the total amount of the (first) pharmaceutical excipient contained in the pharmaceutical dosage form originates from the powdery pharmaceutical composition, i.e. preferably no further (first) pharmaceutical excipient is added in the course of manufacturing the pharmaceutical dosage form from the powdery pharmaceutical composition.

In a preferred embodiment, the pharmaceutical dosage form contains the pharmaceutical composition in such an amount that the content of the (first) pharmaceutical excipient is within the range of from 1.0 to 20 wt.-%, more preferably 2.0 to 18 wt.-%, still more preferably 4.0 to 16 wt.-%, yet more preferably 6.0 to 14 wt.-%, most preferably 7.0 to 13 wt.-%, and in particular 8.0 to 12 wt.-%, relative to the total weight of the pharmaceutical dosage form.

Another aspect of the invention relates to a method for the preparation of a powdery pharmaceutical composition comprising a pharmaceutical excipient, preferably first pharmaceutical excipient, more preferably polyalkylene glycol, and a pharmaceutical component, preferably second pharmaceutical excipient, more preferably α-tocopherol, wherein the temperature profile in the extruder is adjusted so that the composition exits the extruder in form of a cohesive extrusion strand that is optionally grinded to a powder subsequently.

According to this embodiment, the heating zones of the extruder are preferably set at temperatures avoiding the congealing of the extruded material within the extruder. Preferably, extrusion is performed at a temperature slightly above the congealing temperature so that upon the extruder, the extruded material immediately congeals in the course of its cooling in the ambient air. Preferably, the extrusion temperature is at most 10° C. above the melting point/range of the pharmaceutical excipient, more preferably at most 8.0° C., still more preferably at most 6.0° C., yet more preferably at most 4.0° C., most preferably at most 2.0° C. and in particular at most 1.0° C. above the melting point/range of the pharmaceutical excipient, preferably first pharmaceutical excipient, more preferably polyalkylene glycol.

In a preferred embodiment, the composition exits the extruder in form of flocs. This can be achieved by adjusting the temperature profile and the content of the pharmaceutical component, preferably second pharmaceutical excipient, more preferably α-tocopherol, in the pharmaceutical composition.

The invention is further illustrated by the following examples which, however, are not to be construed as limiting its scope.

EXAMPLE 1

PEG 6000 (98.8%) was melted in a beaker at 70° C. α-tocopherol (1.2%) was added to the melt and mixed until a homogeneous melt was formed. The melt was fed into heating zone 3 of an extruder (Leistritz ZSE 18 HP PH 40-D). Heating zones 2 and 3 of the extruder were heated to 70° C. in order to avoid congealing of the melt in the course of the feeding step. Starting at heating zone 4, all other heating zones of the extruder were adjusted to a temperature of 15° C. to ensure congealing of the melt and transportation of the congealed material within the extruder:

| | |
|---|---|
| Heating zone 1 | 25° C. |
| Heating zone 2 | 70° C. |
| Heating zone 3 | 70° C. |
| Heating zone 4 | 15° C. |
| Heating zone 5 | 15° C. |
| Heating zone 6 | 15° C. |
| Heating zone 7 | 15° C. |
| Heating zone 8 | 15° C. |
| Heating zone 10 | 15° C. |
| Heating zone 11 | not heated, because no extrusion die was utilized |
| screw speed | 50 rpm |
| screw configuration | medium shear screw |
| feeding point of melt | in heating zone 3 |

The congealed melt was comminuted due to the revolution of the extruder screws and the resultant shear. The produced powder was collected at the extruder exit.

The yielded particles did neither tend to adhere to one another nor to form agglomerates. They were further ground by means of a coffee mill (Bosch MKM 6000).

EXAMPLE 2

The experiment as described in Example 1 was repeated with six different concentrations of α-tocopherol:

| Ex. | Content of α-tocopherol in melt | PEG 6000 | α-tocopherol |
|---|---|---|---|
| 2-1 | 1.5% | 98.5 g | 2.5 g |
| 2-2 | 5.0% | 95.0 g | 5.0 g |
| 2-3 | 10.0% | 90.0 g | 10.0 g |
| 2-4 | 15.0% | 85.0 g | 15.0 g |
| 2-5 | 20.0% | 80.0 g | 20.0 g |
| 2-6 | 25.0% | 75.0 g | 25.0 g |

The relative α-tocopherol content (%) in the melt, in the product exiting the extruder (extrudate) and in the powder after further grinding by means of the coffee mill was measured (n=3):

| [rel. %] | melt | extrudate | after milling |
|---|---|---|---|
| 2-1 | 101.77 | 102.34 | n.d. |
| 2-2 | 98.76 | 97.30 | n.d. |
| 2-3 | 100.41 | 98.03 | 97.35 |
| 2-4 | 101.45 | 99.61 | 94.91 |

Under the chosen experimental conditions, α-tocopherol contents of up to 5 wt.-% in the melt of PEG 6000 did not require a subsequent grinding and sieving. At α-tocopherol contents above 5 wt.-% and below 15 wt.-%, subsequent grinding and sieving seemed appropriate in order to achieve finer particle sizes. At α-tocopherol contents above 15 wt.-%, a powdery granulate was obtained with a pronounced tendency of adherence. The addition of 50% polyethylene oxide (Mw 7 Mio) improved the properties of the powder after milling in a coffee mill.

EXAMPLE 3

A homogeneous melt was formed from PEG 6000 and α-tocopherol (14 wt.-%). The melt was kept for 100 min at a temperature of 70° C. Every 20 min, a portion of the melt was fed to the extruder in the method as described above. This resulted in 6 testing points that we subjected to analytical investigation. The relative α-tocopherol content (%) in the melt, in the product exiting the extruder (extrudate) and in the powder after further grinding by means of the coffee mill was measured (n=3) for each testing point:

| [rel. %] | melt | extrudate | after milling |
|---|---|---|---|
| 3-1 (0 min) | 98.50 | 98.45 | 97.48 |
| 3-2 (20 min) | 98.43 | 98.50 | 99.18 |
| 3-3 (40 min) | 98.30 | 97.56 | 98.86 |
| 3-4 (60 min) | 98.36 | 98.48 | 98.42 |
| 3-5 (80 min) | 99.16 | 98.26 | 98.30 |
| 3-6 (100 min) | 98.18 | 98.56 | 98.49 |

EXAMPLE 4

The experiment of example 3 was repeated at a α-tocopherol concentration of 4 wt.-%:

| [rel. %] | melt | extrudate | after milling |
|---|---|---|---|
| 4-1 (0 min) | 101.27 | 101.14 | 100.58 |
| 4-2 (20 min) | 101.50 | 101.81 | 101.14 |
| 4-3 (40 min) | 101.86 | 101.10 | 101.58 |
| 4-4 (60 min) | 102.53 | 102.24 | 102.51 |
| 4-5 (80 min) | 102.38 | 101.85 | 102.32 |
| 4-6 (100 min) | 101.29 | 102.04 | 100.92 |

The above experiments demonstrate that α-tocopherol did not significantly degrade.

EXAMPLE 5

PEG 6000 (86 wt.-%) was melted in a beaker at 70° C. α-tocopherol (14 wt.-%) was added to the melt and mixed until a homogeneous melt was formed. The melt was fed into heating zone 3 of an extruder (Leistritz ZSE 18 HP PH 40-D). The melt was transported by means of the rotating screws in the extruder through the adjusted temperature profile. Finally, the melt arrived at the extruder exit that was equipped with a die having a multitude of holes (hole diameter 1 mm each). The melt passed the holes at a temperature slightly above the concealing temperature. The extruder was linked to a micropelletizer and its rotating blades cut the extruded strand. The resultant pellets were collected and ground by means of a coffee mill (Bosch MKM6000).

EXAMPLE 6

Example 5 was successfully repeated with a melt of PEG 6000/α-tocopherol containing 4 wt.-% of α-tocopherol.

The invention claimed is:

1. A method for the preparation of a powdery pharmaceutical composition comprising a homogeneous mixture of (i) polyethylene glycol and (ii) a tocopherol component, wherein the relative weight ratio of the polyethylene glycol to the tocopherol component is within the range of from 1000:1 to 5:1; said method comprising the step of
   (b) extruding a homogeneous mixture of said polyethylene glycol and said tocopherol component in an extruder at a temperature profile allowing a liquid melt of the mixture to congeal to form a congealed mixture in the extruder and the congealed mixture to exit the extruder in form of a powder.

2. The method according to claim 1, comprising the preceding step of
   (a) mixing said polyethylene glycol with said tocopherol component outside the extruder and then feeding the resultant mixture into the extruder;
   feeding said polyethylene glycol and said tocopherol component into the extruder at different feeding points, where the feeding point for said polyethylene glycol is located upstream with respect to the feeding point for said tocopherol component, or vice versa.

3. The method according to claim 2, wherein in step (a) the tocopherol component is dissolved in molten polyethylene glycol, or vice versa.

4. The method according to claim 1, comprising the subsequent step(s) of
   (c) grinding the powder; and
   (d) optionally, grading the powder.

5. The method according to claim 1, wherein in step (b) the temperature profile comprises a temperature gradient of temperature $T_1$ to temperature $T_2$, where $T_1 > T_2$ and where
   $T_1$ is above the melting point/range of the polyethylene glycol and/or the tocopherol component; and/or
   $T_2$ is below the melting point/range of the polyethylene glycol and/or the tocopherol component.

6. The method according to claim 5, wherein
   $T_1$ is within the range of from 25° C. to 115° C.; and/or
   $T_2$ is within the range of from −20° C. to 50° C.

7. The method according to claim 1, which does not comprise any spray congealing or spray drying step.

8. The method according to claim 1, wherein the powder has an average particle size of at most 100 μm.

9. The method of claim 1, wherein said pharmaceutical composition is a pharmaceutical dosage form.

10. The method according to claim 9, wherein the pharmaceutical dosage form has a breaking strength of at least 400 N.

11. The method according to claim 2, comprising the subsequent step(s) of
    (c) grinding the powder; and
    (d) optionally, grading the powder.

* * * * *